United States Patent
Micheletti et al.

(10) Patent No.: US 11,459,507 B2
(45) Date of Patent: Oct. 4, 2022

(54) PROCESS FOR THE CONVERSION OF PLASTICS INTO OLEFINS

(71) Applicant: NEXTCHEM S.P.A., Milan (IT)

(72) Inventors: Francesco Micheletti, Arzignano (IT); Valerio Coppini, Meda (IT)

(73) Assignee: Nextchem S.p.A., Milan (IT)

( * ) Notice: Subject to any disclaimer, the term of this patent is extended or adjusted under 35 U.S.C. 154(b) by 0 days.

(21) Appl. No.: 17/273,394

(22) PCT Filed: Aug. 9, 2019

(86) PCT No.: PCT/EP2019/071415
§ 371 (c)(1),
(2) Date: Mar. 4, 2021

(87) PCT Pub. No.: WO2020/048729
PCT Pub. Date: Mar. 12, 2020

(65) Prior Publication Data
US 2021/0340446 A1  Nov. 4, 2021

(30) Foreign Application Priority Data
Sep. 4, 2018 (IT) .......................... 102018000008335

(51) Int. Cl.
C10B 53/00 (2006.01)
C07C 2/82 (2006.01)
(Continued)

(52) U.S. Cl.
CPC .............. *C10B 53/07* (2013.01); *C10G 47/02* (2013.01); *C10G 57/02* (2013.01); *C10G 2300/1003* (2013.01)

(58) Field of Classification Search
None
See application file for complete search history.

(56) References Cited

U.S. PATENT DOCUMENTS 4,064,156 A    12/1977 McRobbie
6,096,934 A *  8/2000  Rekoske ................. C07C 9/06
                                              585/824
(Continued)

FOREIGN PATENT DOCUMENTS

EP    0089105 A2    9/1983
WO    2011004251 A1  1/2011

OTHER PUBLICATIONS

Brems et al., "Gasification of plastic waste as waste-to-energy or waste-to-syngas recovery route", Natural Science, vol. 5, No. 6, 695-704 (2013). (Year: 2013).*

(Continued)

*Primary Examiner* — Philip Y Louie
(74) *Attorney, Agent, or Firm* — Patterson Intellectual Property Law, P.C.

(57) ABSTRACT

Process for the conversion of plastics to olefins comprising the following steps: A) gasification of the plastics to synthesis gas by reaction of the plastics with pure oxygen; B) catalytic conversion of the synthesis gas produced in stage A) to methane in at least three successive stages, in each of which hydrogen is added; C) catalytic conversion of the methane produced in stage B) into olefins by the oxidative coupling reaction of methane; and D) separation of the olefins produced in stage C) from other compounds present in the reaction mixture of said stage C).

20 Claims, 2 Drawing Sheets

(51) Int. Cl.
*C07C 1/12* (2006.01)
*C07C 2/84* (2006.01)
*C07C 1/04* (2006.01)
*C10B 53/07* (2006.01)
*C10G 47/02* (2006.01)
*C10G 57/02* (2006.01)

(56) References Cited

U.S. PATENT DOCUMENTS

| | | | |
|---|---|---|---|
| 2016/0194573 A1* | 7/2016 | Chapman | C10K 3/04 |
| | | | 585/324 |
| 2018/0169561 A1 | 6/2018 | Jonnavittula et al. | |
| 2018/0215682 A1 | 8/2018 | Humera et al. | |

OTHER PUBLICATIONS

International Searching Authority: Search report for co-pending patent application No. PCT/EP2019/071415 dated Sep. 11, 2019, 13 pages.

\* cited by examiner

PROCESS FOR THE CONVERSION OF PLASTICS INTO OLEFINS

The present invention relates to a process for the conversion of plastics into olefins, in particular for the conversion of recycled plastics.

BACKGROUND

The disposal of plastic is an important environmental problem, given the large amount of plastic waste produced both domestically and on an industrial level, especially in the most industrialized countries. Although most of the plastic that has arrived at the end of its use currently has the most important disposal in landfills or is directly abandoned in the environment, today some technologies and processes to try to solve the problem of plastic disposal. The problem is addressed, with various approaches and various technologies, including combustion, the remelting of plastic for the production of new objects, and biodegradation, if the plastic is biodegradable. However, it is known that only a relatively small part of the plastic currently produced is biodegradable.

Each of the approaches mentioned above results in a loss of value of the product obtained after the conversion with respect to the value of the original plastic. This is evident in the case of combustion, considering that in this technology the plastic is simply used as a fuel, and also of biodegradation, considering that the product obtained from biodegradation is used in applications of little economic value, for example as a soil improver in agriculture, or, with further conversions, as solid fuel. However, even in the case of the remelting of plastic for the production of objects, there is a loss of value, since the object obtained from recycled plastic is used in an application of lower value than the original one.

Processes are also known for the conversion of recycled plastic to synthesis gas (syngas), which then finds various applications, both as a fuel and as a raw material for chemical syntheses, for example in the Fischer-Tropsch process, or—thanks to its content of hydrogen—in the synthesis of ammonia or in the production of electricity in fuel cells. The molar ratio of hydrogen/carbon monoxide ($H_2/CO$) in known processes is usually less than 1, which indicates that the synthesis gas obtained is low in hydrogen and not suitable for the production of products such as methanol, ammonia and derivatives thereof, with the consequence that the prevalent use of synthesis gas is still the use as a fuel.

None of the aforementioned technologies is able to return plastic to its original value, since it is obviously not possible to convert recycled plastic into virgin plastic.

In addition to the loss of value, the recycled plastic conversion products obtainable with current technologies largely concern sectors other than that of the original plastic, such as: i) in the case of combustion, energy production; ii) in the case of biodegradable plastic, the agricultural sector or solid fuels; iii) in the case of the conversion into synthesis gas, again the production of energy or other chemical products derived from the synthesis gas.

Therefore, every year there is a significant loss of virgin plastic, which entails the need to produce new plastic to replace the part lost in the environment, constituting the vast majority, and the part converted into other products, intended for applications other than those of the original plastic. Furthermore, the production of new plastic weighs on the availability of fossil resources, which are the raw material used for the production of plastic.

EP 0089105 A2 discloses a multi stage methanation process for the production of fuel gases suitable as substitute natural gas (SNG) from synthesis gases obtained by the gasification of oils and coal.

US 2018/2125682 discloses methods for producing hydrocarbons, which comprise directing a feed stream including methane and an oxidizing agent into an oxidative coupling of methane (OCM) unit to generate an OCM effluent comprising the hydrocarbon compounds.

US 2018/169561 A1 discloses a method for producing higher hydrocarbons comprising introducing methane and an oxidant into a reactor for the oxidative coupling of methane (OCM).

None of the documents above deals with gasification and/or recycling of plastics.

In this context, the technical task of the present invention is to provide a process for the conversion of plastics which eliminates or reduces the drawbacks of the known systems mentioned above.

In particular, an object of the present invention is to provide a process for the conversion of plastics into olefins, so that such olefins can be used in polymerization processes for the new production of polyolefins.

Another object of the present invention is to provide a process for the conversion of plastics into olefins maximizing the olefin yield, i.e. minimizing the loss of the carbon contained in the initial plastic due to the formation of undesired compounds or in any case not useful for obtaining olefins, especially considering that the process involves more stages, and therefore the final yield depends on the yield of each individual stage.

SUMMARY OF THE INVENTION

The aforementioned and other objects and advantages of the invention, as will emerge from the following description, are achieved with a process for the conversion of plastics to olefins comprising the following stages:

A) gasification of the plastics to synthesis gas by reaction of the plastics with the addition of pure oxygen, said pure oxygen being used in a quantity such that, added to the amount of oxygen possibly present in said plastics and measured with ASTM D5291_A, forms an amount of total oxygen ranging from 40 to 65 molar % with respect to the amount of stoichiometric oxygen required for the conversion of all the carbon contained in the plastics to $CO_2$;

B) catalytic conversion of the synthesis gas produced in said stage A) to methane in at least three successive stages, in at least the first two of which hydrogen having a degree of purity of ≥95% is added to the synthesis gas;

C) catalytic conversion of the methane produced in said stage B) into olefins by the oxidative coupling reaction of methane; and D) separation of the olefins produced in said stage C) from other compounds present in the reaction mixture of said stage C).

DETAILED DESCRIPTION

The invention will now be described with reference also to the accompanying figures, given by way of non-limiting example, in which.

Figure 1:
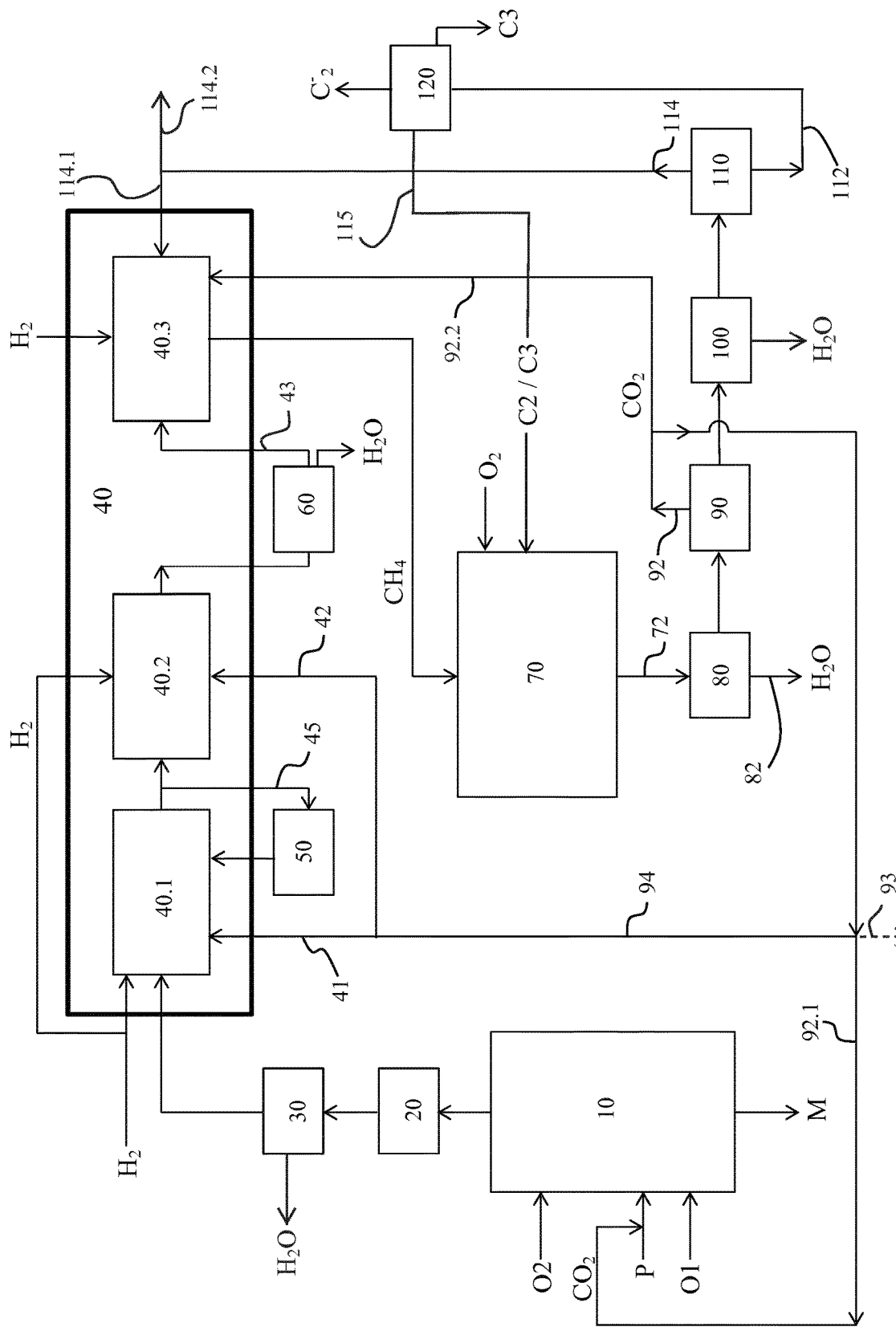
FIG. 1 shows a general block diagram of the process according to the invention.

In the present description, the term "plastics" refers to a material based on organic macromolecules composed mainly of carbon and hydrogen, such as polyolefins, or also comprising oxygen, such as polyesters, polyethers, acrylic and methacrylic polymers, polyacetals, or macromolecules also comprising nitrogen, such as polyamides and polyurethanes, or macromolecules also comprising halogens, such as polyvinyl chloride and fluorinated polymers, or sulfur-containing macromolecules, such as polysulfides and polysulfones, or copolymers obtained by combining various monomers, such as acrylonitrile-butadiene copolymers (ABS) and like.

Typically, the plastics used in the present process are recycled plastics, i.e. recovered from household and/or industrial waste by appropriate mechanical selection and grinding operations, as is known in the art. It therefore also contains various additives and other components used in the production of the articles from which the recycled plastic derives.

To maximize the efficiency of the process it is preferable that the carbon content in the plastic used is high, considering that the whole process is finalized to the conversion of such carbon into olefins.

Preferably, the carbon content of the plastic used is greater than 45% by weight, more preferably it is greater than 60% by weight, even more preferably it is greater than 70% by weight.

Preferably, the hydrogen content of the plastic used is greater than 5% by weight, more preferably it is greater than 8% by weight, even more preferably it is greater than 12% by weight.

Preferably, the oxygen content is less than 20% by weight, more preferably it is less than 10% by weight, even more preferably it is less than 7% by weight.

Preferably, the content of nitrogen, halogens and sulfur is overall less than 3% by weight, more preferably it is less than 2% by weight, even more preferably it is less than 0.5% by weight.

Preferably, the inert content of the plastic used is less than 20% by weight, more preferably it is less than 5% by weight, even more preferably it is less than 3% by weight.

Preferably, the moisture content of the plastic used is less than 10% by weight, more preferably it is less than 5% by weight, even more preferably it is less than 2% by weight.

Plastics consisting mainly of polyolefins, therefore with low or zero heteroatoms content, are preferred since they are made of a starting material having a very high carbon content, whose balance to 100% is almost entirely composed of hydrogen. Plastics consisting of polyethylene or polypropylene, or mixtures thereof, are particularly preferred.

The plastics intended for use in the present process are then previously selected, shredded and reduced to flakes, for optimal use in the first process stage, which is the gasification stage.

Stage A)

The stage of gasification of plastics is, in general, a known process since it is already used for the production of synthesis gas, mainly from coal and biomass, but also, more recently, from plastics. However, in order to produce high yield olefins, in accordance with the final objective of the present process, it is advantageous that the process is conducted under certain conditions, defined below.

In the process of the invention, the synthesis gas essentially consists of a mixture of CO and $H_2$, with a reduced $CO_2$ and $H_2O$ content. Depending on the nature of the plastic used, nitrogen, sulfur compounds and halogenated compounds may be present, whose presence can be avoided or at least reduced with an appropriate selection of the starting material.

The process is an oxidative process of an autothermal and non-catalytic type, i.e. the reactions that lead to the formation of the synthesis gas take place by means of only the heat produced by the reactions themselves, which are partial oxidation reactions in order to maximize the yield in CO and $H_2$.

According to an aspect of the process, the oxidation is carried out with pure oxygen in sub-stoichiometric quantity with respect to carbon.

In particular, the total oxygen quantity, both present in the plastics and added as a comburent, may range from 40 to 65% molar with respect to the quantity of stoichiometric oxygen, i.e. the amount of oxygen necessary for complete combustion of the carbon (i.e. 1 mole $O_2$/mole C). More preferably, this amount of oxygen is in the range of 45-55% with respect to the stoichiometric amount.

The amount of oxygen possibly present in the plastics ($O_{PLASTICS}$) is measured according to ASTM D5291-A, in which the percentage of oxygen is calculated by difference from the percentage of the other components, e.g. C, H, N.

The amount of oxygen to be added is thus calculated with the following formula:

$$O_{ADDED} = O_{TOT} - O_{PLASTICS}$$

wherein $O_{TOT}$ is the total amount of oxygen, within the range 40 to 65% molar of the stoichiometric amount of oxygen required for reaching a complete combustion of the whole carbon contained in the plastics, namely the amount of oxygen required to converting it to $CO_2$;

$O_{PLASTICS}$ is the total amount of oxygen contained in the plastics, measured as defined above;

$O_{ADDED}$ is the amount of oxygen to be introduced in the gasification reactor.

The term "pure oxygen" means a gas containing at least 95% by weight of oxygen, preferably at least 97% by weight of oxygen, more preferably at least 99% by weight of oxygen. This means that for step A) the process of the invention does not use air, which contains about 78% molar of nitrogen and only 21% molar of oxygen.

The process is conducted with a temperature profile between 600-2000° C. and a pressure slightly above atmospheric pressure. Preferably, the pressure is between 0.10-0.12 MPa. The high temperature allows the breakage of long macromolecular chains.

The granules of plastics are fed to the reaction in the presence of a flow of carbon dioxide, coming from the process stages placed downstream of the gasification. In these stages, a quantity of carbon dioxide is produced which is sufficient for supply to stage A), without the need for external supply. This amount of carbon dioxide is produced in particular as a by-product in the oxidative methane coupling stage C).

The introduction of pure $O_2$, rather than air or enriched air, as in conventional processes, involves a considerable reduction in the quantity of nitrogen to be purged from stage D, more precisely from the cryogenic separation section, described below, and, consequently, of the carbon loss associated with such purge.

Figure 2:
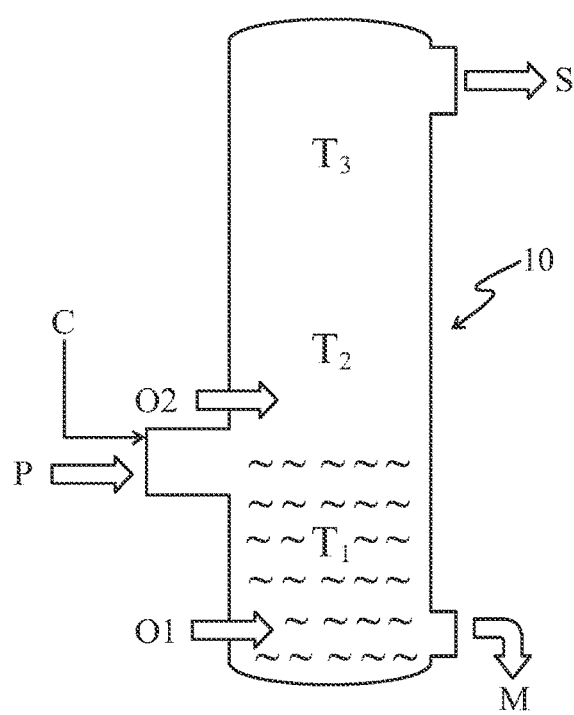
FIG. 2 is a schematic view of a reactor for stage A) of the process.

With reference to FIG. 2, a reactor 10 for carrying out the gasification of plastics according to stage A) is schematically shown, according to an embodiment of the present invention.

The plastic is introduced into an intermediate zone of the reactor, as indicated by the arrow P, through a loading hopper together with carbon dioxide, which is introduced as indicated by the arrow C. Carbon dioxide has the function of making the plastic inert, that is, eliminating or reducing the quantity of air—and therefore of nitrogen—entrained in the reactor 10 by the same plastic.

Oxygen is introduced at two different points, as indicated by the arrows O1 and O2 in FIGS. 1 and 2. A first point of introduction of oxygen (O1) is near the bottom of the reactor. At this point 65-80% of the total oxygen is added. The remaining 20-35% is added in a second point (O2), in the intermediate zone of the reactor, in the proximity of the introduction of the plastic. The introduction points O1 and O2 correspond to areas of the reactor where different temperatures are established, as explained below. This way of introducing oxygen helps to avoid the complete combustion of the reagents, which would lead to an increase in the amount of $CO_2$ formed.

As mentioned above, areas with different temperatures are established inside the reactor.

A first temperature zone ($T_1$) is established in the lower part of the reactor, with values ranging between 1600-2000° C., in order to guarantee the complete fusion of the inert fraction present in the waste.

Unreacted molten residues and/or inert materials, typically forming 2-3% by weight of the plastic introduced into the reactor, are deposited at the bottom of the reactor. If the quality of input plastic is lower, due to a less accurate selection process, larger quantities of aggregates, up to 20% by weight, may be formed. These residues are discharged as shown by the arrow M.

A second temperature zone ($T_2$) is established in the intermediate part of the reactor, corresponding to the plastic and oxygen introduction points, with values ranging between 600-1000° C. In this area, the gasification reaction mainly occurs with the formation of the synthesis gas, which moves upwards.

A third temperature zone ($T_3$) is established in the upper part of the reactor, with values ranging between 1000-1200° C. In this area, there is the completion of the cracking of the hydrocarbon molecules/chains, in particular the heavier ones such as tars. From the top of this area the synthesis gases are discharged, according to the arrow S.

By carrying out the gasification as described, the plastic is completely converted to the gaseous phase, with the exception of inert materials or residues of foreign materials, free of tar/carbon residues or other undesired substances.

At the reactor outlet, the synthesis gas is rapidly cooled (quenched), as indicated with reference numeral 20 in FIG. 1, thus blocking the formation of undesired substances.

The synthesis gas produced contains $H_2$ and CO in a molar ratio that mainly depends on the carbon content of the plastics used. If the selection stage upstream of the gasification stage A) is coarser or the starting material is less "valuable", the $H_2$/CO ratio may be less than 1:1, and go down to 0.8:1. The synthesis gas produced also contains a minor fraction of combustion products ($CO_2$ and $H_2O$). In stage A) of the process according to the invention, the synthesis gas produced preferably has a molar ratio $H_2$/CO of 1:1 and even higher, for example also 1.10:1 and up to 1.20:1.

Before being sent to the next stage B) for conversion to methane, also called the "methanation" stage, the cooled synthesis gas is compressed in a compression station 30 (FIG. 1), in which a quantity of water is extracted from the gas. By compression, the pressure of the synthesis gas is raised to values up to 1.5-7.0 MPa.

The synthesis gas is then subjected to usual purification treatments, not described in detail since they are known, such as: elimination of any entrained solids, acid and alkaline washing, removal of chlorides and sulfides, which could poison the methanation catalyst.

It is also preferable to insert a gasometer upstream of the methanation stage, acting as a buffer and reducing the fluctuations of flow rate and composition of the synthesis gas produced in stage A).

In an example of embodiment of the gasification stage A) according to the process of the present invention, it was the recycled plastic having the composition shown in Table 1 below.

TABLE 1

| Waste Plastic Composition | | |
|---|---|---|
| C | % weight | 79.5% |
| H | % weight | 13.1% |
| N | % weight | 0.2% |
| S | % weight | 0.1% |
| Cl | % weight | 0.0% |
| O | % weight | 4.5% |
| Water | % weight | 0.7% |
| Ashes | % weight | 1.9% |

The synthesis gas produced with the process of stage A) had the composition shown in the following Table 2.

TABLE 2

| Gas Composition from Waste Plastic Gasification | | |
|---|---|---|
| $H_2$ | % mol | 53.48% |
| CO | % mol | 45.61% |
| $CO_2$ | % mol | 0.07% |
| $H_2O$ | % mol | 0.16% |
| $N_2$ | % mol | 0.02% |
| Ar | % mol | 0.02% |

The embodiment of stage A) shows that it was possible to obtain a synthesis gas with a high $H_2$/CO ratio, in particular a ratio of 1.17. This is particularly advantageous since it allows reducing the quantity of hydrogen required for the subsequent stage B). Furthermore, the amount of nitrogen is very low, contrary to what happens in processes that use air or enriched air. Finally, the amount of nitrogen is low also thanks to the use of $CO_2$ to neutralize the plastic entering the stage A).

Stage B)

The compressed synthesis gas obtained from the gasification stage A), possibly purified, is sent to stage B) of catalytic methanation, indicated with reference numeral 40 in FIG. 1.

In this stage, methane is produced from hydrogen and carbon oxides (CO, $CO_2$), according to the following reaction stoichiometries, in the gas phase:

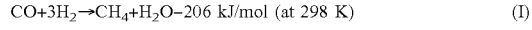

$$CO+3H_2 \rightarrow CH_4+H_2O-206 \text{ kJ/mol (at 298 K)} \quad (I)$$

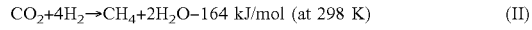

$$CO_2+4H_2 \rightarrow CH_4+2H_2O-164 \text{ kJ/mol (at 298 K)} \quad (II)$$

Reactions (I) and (II) are characterized by favoured thermodynamic equilibrium, i.e. shifted towards the products, in the following conditions:

high pressure, obtained by compressing the gas upstream of the reactor, preferably between 2.5 and 7 MPa;

increase of $H_2$ in the reagent gases, obtained by adding hydrogen from an external source; for example, coming from steam-reforming or electrolysis or cracking units available at the site where the process is carried out;

temperature control, obtained with appropriate cooling, required by the exothermic nature of the methanation reactions;

elimination of $H_2O$ from the reaction products, obtained by condensation.

The methanation reaction, i.e. the conversion of the synthesis gas into methane, is a catalytic reaction.

The catalysts used are known to those skilled in the art. Typically, catalysts based on Ni and other metals are used, such as Ru, Rh, Pt, Fe and Co. In general, these are supported catalysts.

The most widespread catalysts are composed of Ni supported on alumina, capable to ensure good activity and selectivity, resulting in being the cheapest.

Examples of commercial catalysts for the methanation of synthesis gases are as follows:

CRG™, marketed by Johnson-Matthey;

MCR-2X, MCR-8, marketed by Haldor-Topsoe.

The strong exothermic nature of the reaction is a critical factor, which therefore requires adequate temperature control, essential for maintaining the equilibrium of the methanation reaction towards the products, avoid undesired reactions and protect the catalyst from thermal stress which could cause the deactivation thereof.

Therefore, temperature control takes place according to various operating modes, in particular:

By performing the methanation in at least three stages in series, indicated in FIG. 1 with 40.1, 40.2, 40.3, with intermediate cooling (50, 60) between the various stages, with heat recovery and steam production.

By feeding fresh hydrogen in at least the first two of said three stages.

By recycling most of the gaseous mixture produced in the first reactor, also comprising the methane produced, to the same first reactor, as indicated by line 45 of FIG. 1.

The recycle ratio, or the ratio between:

the outgoing mixture rate produced in the reactor of stage 40.1 which is recycled, after compression, and the net flow rate at the second stage 40.2 is in the range 4-20, more preferably in the range 8-18.

In an even more preferred embodiment, the recycle ratio ranges from 14 to 16, for example it is about 15. In this case, the outgoing mixture flow rate produced in the reactor of stage 40.1 which is recycled, after compression, is about 15 times the net flow rate that advances and is fed to the reactor of stage 40.2.

In the following description, the three methanation stages 40.1, 40.2 and 40.3 also indicate without distinction the three reactors in which the methanation is carried out.

With reference to the recycling of gas from the outlet of the first stage, in FIG. 1, reference numeral 50 indicates as a whole the units provided for the cooling and compression of the gas produced in the first methanation stage 40.1. Such a compressed gas is reintroduced in the first stage 40.1, as indicated by the line 45, to carry out a dilution of the reactants CO, $CO_2$ and $H_2$ by the methane produced. Although an increase in the concentration of the product ($CH_4$) shifts the equilibrium towards the reactants, the need for temperature control prevails over the thermodynamic considerations concerning the consequent shift of the equilibrium of (I) and (II) towards the left side.

As already highlighted in the previous paragraph, the stoichiometry of reactions (I) and (II), according to which the total conversion to $CH_4$ requires:

3 moles of $H_2$ per mole of CO 4 moles of $H_2$ per mole of $CO_2$ involves the need for a further supply of hydrogen from an external source (e.g. steam-reforming or electrolysis or cracking units) in order to compensate for the $H_2$ deficiency in the synthesis gas, containing 0.8-1.2 mol of $H_2$ per mol of C. Hydrogen from an external source has a purity of equal to or greater than 95%. Preferred external sources of hydrogen are renewable sources, such as electrolysis. The degree of purity of hydrogen is measured with ASTM D7941M-14.

This flow rate of hydrogen from an external source is 1.5-3.5 mol of $H_2$ per mol of C entering the stage B), preferably 2.0-3.0 mol $H_2$ per mol of C entering. This excess of $H_2$ is useful to shift the balance of the methanation reactions (I) and (II) towards the right and therefore towards the conversion of CO and $CO_2$ into methane.

Therefore, wishing to satisfy both the following conflicting requirements, i.e. i) the already highlighted need to check exothermicity of reactions (I) and (II), in particular at the first stage (40.1) where the conversion is greater; ii) the need to limit the unconverted hydrogen output in stage B), which is found (undesired) to be fed to the next stage C); it is advantageous to split the supply of hydrogen from an "external" source between the first two stages of methanation 40.1 and 40.2.

In the process of the invention, the supply of the hydrogen required for carrying out the methanation reactions (I) and (II) is split between the first two reactors 40.1 and 40.2.

This "external" hydrogen is then split between the aforementioned stages according to the criterion of making the (adiabatic) temperature increases of the various stages more homogeneous. In general, the hydrogen sent to the first stage 40.1 constitutes 65-100% of the total hydrogen sent to the section, preferably 75-95%, more preferably 85-90% of the total hydrogen sent to the section.

The adopted process scheme contemplates the use of at least three adiabatic fixed-bed reactors with intermediate cooling, recycling of compressed gas and introduction of fresh hydrogen between the various stages.

In one embodiment, four stages of methanation in series are provided, with intermediate cooling, recycling of compressed gas and introduction of fresh hydrogen at the various stages. The methane-containing gas produced in the first reactor is partly recycled in the unit itself, after compression, as for the arrangement in three stages.

The diluting effect of recycled methane contributes to temperature control. With the addition of fresh hydrogen to at least two reaction stages, in the case where stage B) comprises three stages of methanation, or at least three reaction stages, in the case where stage B) comprises four stages of methanation, the $H_2$/CO ratio of the synthesis gas is increased from 1:1 to 2.5-3.5:1, favouring the conversion to methane. The heat output from each stage is used to produce superheated steam.

In one embodiment, the methanation reactors of stages 40.1, 40.2 and 40.3 are operated at 2.5-3.0 MPa. The inlet and outlet temperatures at each stage are respectively 250° C. and 300-450° C., eliminating the risk of deactivation of the catalyst which does not operate above 500° C.

It should be noted that the concentration of the CO at the first stage inlet 40.1 is lower than the concentration of $CO_2$ due to the effect of large recycling and the lower reactivity of $CO_2$ compared to CO. It should also be noted that all stages exhibit a very large dilution in methane.

It is possible to send to the methanation stages 40.1 and 40.2 a current rich in $CO_2$ coming from the subsequent process stages (in particular from stage D), unit 90—$CO_2$ removal-represented in FIG. 1), through lines 41 and 42, as discussed below.

It should be noted that, if the case in which the methanation unit (stage B) must shall process these additional streams, the flowrate of $H_2$ from an external source must necessarily take into account the additional $CO_2$ content supplied by these streams.

After the penultimate methanation stage, therefore, with reference to FIG. 1, downstream of the methanation stage 40.2, a condensation 60 is prepared to remove the water before sending the mixture to a final methanation stage 40.3.

The function of this last methanation stage is to improve the efficiency of the conversion of carbon into methane. In the last stage of methanation, the conversion of substantially all the CO generated in stage C) and a part of the $CO_2$ co-product, in methane, is carried out according to the reactions (I) and (II) described above.

These reactions require $H_2$ from various sources inside and outside the process is used. By the term "sources inside the process" it is meant, for example, the subsequent stage C) of oxidative coupling for the formation of olefins, as well as $H_2$ already present in stream 43, deriving from the incomplete conversion of $H_2$ in the methanation stage 40.2. By "sources outside the process" it is meant hydrogen generated by electrolysis, steam reforming or steam cracking.

For the latter methanation stage 40.3, methane, CO, $CO_2$ and hydrogen from downstream stages are also fed to the reactor, where the separation of the olefins from other compounds still present in the final mixture takes place, after oxidative coupling. In particular, 92.2 indicates the $CO_2$ recycling line and 114.1 the recycling of the cryogenic separation section 110 (described below in stage D), consisting mainly of methane and relatively minor amounts of CO and nitrogen.

In fact, in the final methanation unit 40.3, $H_2$ and CO are combined:
  with additional $CO_2$ (from the $CO_2$ removal unit);
  with $CH_4$ recycling (with CO, hydrogen and nitrogen) from cryogenic separation;
  (any) additional $H_2$;
to be converted into methane for optimal conversion to olefins in the next stage.

The last methanation unit 40.3 is designed so as to: i) maximize the consumption of hydrogen, which would react with oxygen in the methane oxidative coupling reaction (stage C), competing with the desired reaction; ii) eliminate the CO; iii) convert CO and $CO_2$ into methane as much as possible.

According to an aspect of the present process, the last methanation stage is carried out with a molar ratio $H_2/C$ of between 1.2 and 3, preferably between 1.5 and 2.5.

Figure 3:
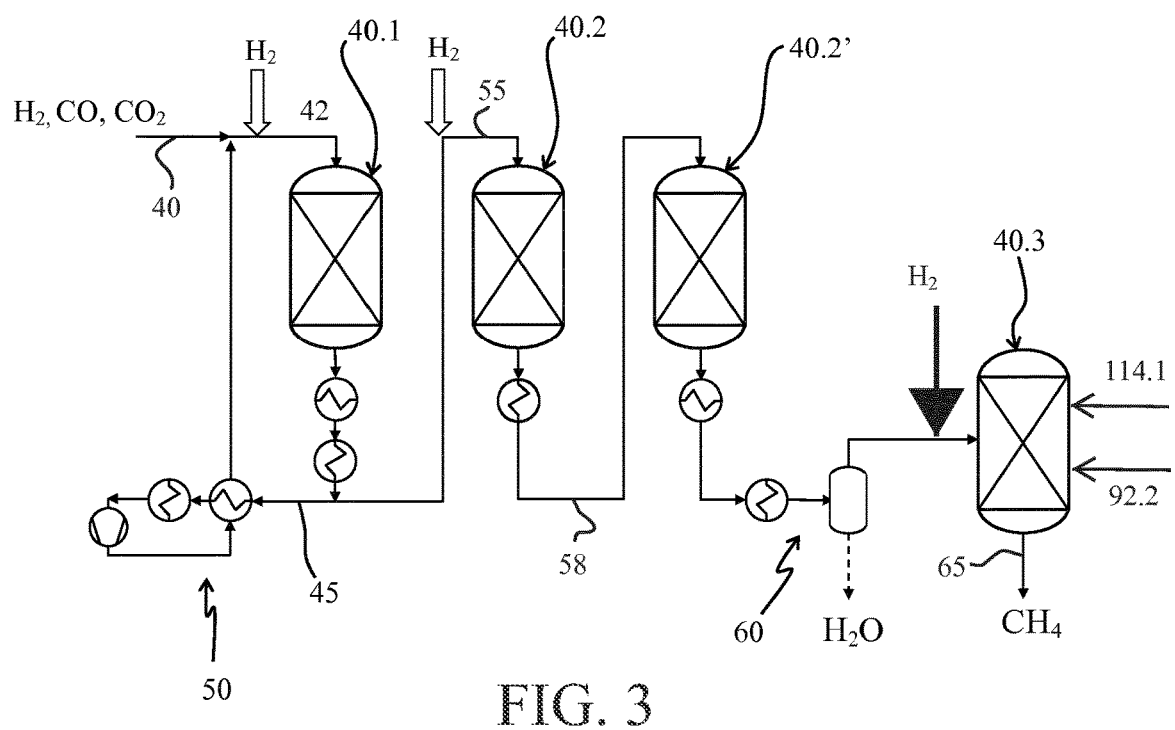
FIG. 3 is a diagram of an embodiment of stage B) of the process.

FIG. 3 shows a diagram of the methanation stage in the embodiment comprising four successive stages of methanation in series 40.1, 40.2, 40.2' and 40.3.

As described in relation to the three-stage embodiment, the mixture leaving the first stage 40.1 is partly recycled to the same stage, as indicated by line 45. Similarly to what is shown in FIG. 1, in FIG. 3 reference numeral 50 indicates as a whole the set of units provided for the cooling and compression of the gas produced in the first methanation stage 40.1, which is then reintroduced in the first stage 40.1, as indicated by line 45, to carry out a dilution of the reactants CO, $CO_2$ and $H_2$ by the methane produced.

Similarly, to what is shown in FIG. 1, in FIG. 3, downstream of the third methanation stage 40.2', reference numeral 60 generally indicates the cooling and condensation units, suitable for removing the water before sending the mixture to the last methanation stage 40.3. As mentioned above, this last methanation stage has the function of improving the efficiency of the conversion of carbon into methane, an efficiency further improved also thanks to the additional methanation stage 40.2'.

In an exemplary embodiment of the methanation stage B) in 4 subsequent stages according to the process of the present invention, the input/output compositions of the various stages shown in the following Table 3 are obtained.

TABLE 3

(Stream from FIG. 3)

| STREAM (FIG. 3) Comp. (% mol) | 40 Syngas | 42 1st stage input (40.1) with recycling and addition of $H_2$ | 45 1st stage output (40.1) | 55 2nd stage input (40.2) post addition of $H_2$ | 58 2nd stage output (40.2) | 60 3rd stage output (40.2') (post-condens) | 65 4th stage output (40.3) |
|---|---|---|---|---|---|---|---|
| $H_2$ | 53.5% | 12.9% | 1.9% | 14.7% | 1.6% | 0.4% | 0.4% |
| $CH_4$ |  | 73.1% | 83.4% | 72.6% | 81.4% | 92.4% | 87.1% |
| $CO_2$ | 0.7% | 9.0% | 10.1% | 8.8% | 6.2% | 6.7% | 1.5% |
| CO | 45.6% | 4.6% | 0.4% | 0.3% | traces | — |  |
| $H_2O$ | 0.2% | 0.4% | 4.2% | 3.6% | 10.8% | 0.5% | 6.9% |
| $N_2$ + Ar |  |  |  |  |  |  | 4.1% |

It should be noted that at the output of the third stage (40.2'), the process gas has a very high methane content (92.4% mol). It is also designated as "synthetic natural gas" (SNG).

The final methanation stage (40.3) which, as already noted, must process not only the product of the third methanation stage but also i) recycling of $CH_4$ and ii) recycling of $CO_2$ from successive units (stage D), does not increase the $CH_4$ content but reduces the $CO_2$ content to acceptable levels for the operation of the subsequent OCM reactor (stage C).

Stage C)

The methane obtained in stage B) is catalytically converted into olefins by the methane oxidative coupling reaction.

With reference to FIG. 1, stage C) is indicated with reference numeral 70, indicating also the reactor in which the methane oxidative coupling reaction is carried out. The reactor and its reaction are also designated as "OCM reactor" and "OCM reaction" (Oxidative Coupling of Methane).

The OCM reaction is known and various catalysts suitable for its realization are described in both scientific and patent literature. Such catalysts are also commercially available.

In an OCM process, methane ($CH_4$) reacts with an oxidant acting on a catalyst bed to generate compounds having two or more carbon atoms. For example, methane reacts with oxygen on a catalyst suitable for generating ethylene, according to reaction (III):

$$2CH_4 + O_2 \rightarrow C_2H_4 + 2\,H_2O \quad (III)$$

See, for example, Zhang, Q., *Journal of Natural Gas Chem.*, 12:81, 2003; Olah, G. "*Hydrocarbon Chemistry*", Ed. 2, John Wiley & Sons (2003). The reaction is exothermic ($\Delta H = -67$ kcal/mole) and runs at high temperatures (for example higher than 450° C. or even higher than 700° C.

Several catalysts showed activity for the OCM reaction, including various forms of iron oxide, $V_2O_5$, $MoO_3$, $Co_3O_4$, Pt—Rh, $Li/ZrO_2$, Ag—Au, $Au/Co_3O_4$, Co/Mn, $CeO_2$, MgO, $La_2O_3$, $Mn_3O_4$, $Na_2WO_4$, MnO, ZnO and combinations thereof, on various supports.

Catalysts suitable for carrying out the oxidative coupling according to stage C) are for example catalysts based on mixed metal oxides, as described for example in U.S. Pat. No. 9,334,204 B1 of Siluria Technologies, Inc., USA.

These catalysts allow partial oxidation and the highly selective conversion of methane mainly to ethylene and ethane and, to a lesser extent, propylene and other heavier hydrocarbons.

Figure 4:
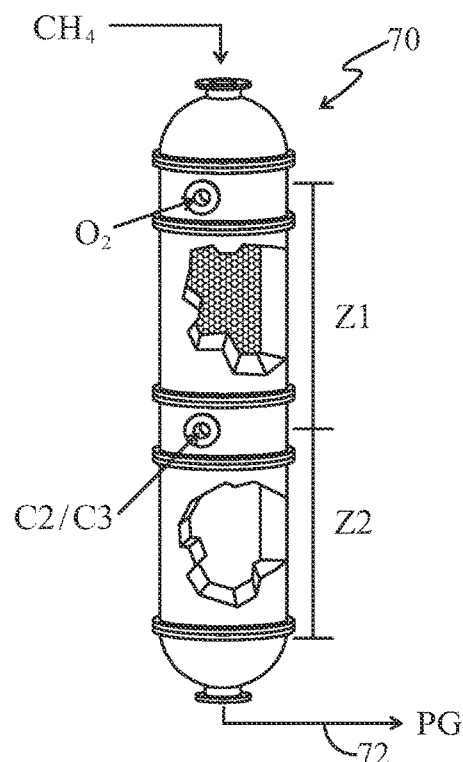
FIG. 4 is a diagram of an embodiment of a reactor for stage C) of the process.

A diagram of OCM reactor for the realization of the stage C) of the process according to the invention is shown in FIG. 4.

With reference to FIGS. 1 and 4, the methane-rich gas coming from the last methanation stage 40.3 is fed to the stage/reactor 70. This supply stream is preheated to about 500° C., in a manner not shown.

According to an aspect of the process of the invention, the stage C) of oxidative methane coupling is carried out using a mixture containing at least 85% molar of methane produced in the previous stage B).

A stream of high purity oxygen (99.5% mol) is fed to the reactor 70, for carrying out the OCM reaction.

A C2/C3 recycling stream from stage D) is also fed to the reactor 70, containing mainly ethane and/or propane, to be converted respectively in ethylene and/or propylene by thermal cracking.

The OCM reactor 70 is a vertical, adiabatic reactor, operating at mild pressure conditions, typically between 0.5-1.2 MPa, preferably between 0.7-1.0 MPa, constructed with conventional materials.

The OCM reactor includes two conversion stages, in the same apparatus.

More particularly, the reactor 70 comprises an upper zone containing the fixed-bed catalyst, designated in FIG. 4 as Z1, in which methane and oxygen are fed. In this zone Z1, the OCM reaction takes place, which is exothermic, i.e. methane is converted to ethylene, and partly also to ethane, propylene and propane.

The reactor also includes a lower zone, designated as Z2, also called "Post Bed Cracking Section" (PBC), where ethane and propane are converted to additional ethylene and propylene by thermal cracking. These reactions are endothermic.

Overall, the OCM stage is highly exothermic. The hot effluent from the OCM reaction section is typically at about 860-880° C. This effluent temperature can, however, drop to about 750° C. if the C2/C3 recycling stream (from stage D), introduced in the lower PBC area of the reactor, is increased. In this case, the endothermic reactions are more relevant, whereby the temperature of the hot effluent drops to 750° C. If the gas containing methane from stage B) which is fed to stage C) contains neither ethane nor propane, although a minimum quantity of ethane is produced as a by-product in the OCM reactor itself, the temperature of the hot output effluent is around 860-880° C.

The hot effluent leaving the OCM reactor 70 is cooled through a series of heat exchangers at a decreasing thermal level, allowing, in order, to: i) produce saturated steam at high pressure; ii) heat the methane flow fed to the OCM reactor, preheat the water for steam production; iii) preheat the feed of the last methanation stage 40.3.

The effluent from stage C) is a gaseous mixture comprising olefins, water, unreacted methane and saturated hydrocarbons.

Stage D)

The gas containing the olefins discharged from the OCM stage 70 through a line 72 (FIGS. 1 and 4), also called process gas (PG), is sent for treatments that include three-unit operations:
a) compression;
b) $CO_2$ removal;
c) water removal.

a) The process gas from the OCM reactor section is compressed using a 3 or 4-stage centrifugal process compressor at a final pressure of 4-5 MPa. Intermediate cooling is carried out in water-cooled tube bundle heat exchangers. These operations are generally designated with reference numeral 80 in FIG. 1. Water and condensed hydrocarbons are discharged via line 82.

b) After compression in units 80, the process gas is directed to a $CO_2$ removal unit 90. It must be removed in a thorough manner i) to avoid freezing in subsequent cryogenic separations and ii) to guarantee compliance with the specification on the maximum $CO_2$ content in the final product (Polymer Grade purity ethylene). The $CO_2$ removal unit uses two distinct processes for $CO_2$ removal: chemical/physical absorption using appropriate organic solvents, such as mono-ethanolamine (MEA), and a caustic wash. The carbon dioxide thus removed from the process gas is partially recycled with the line 92 to the last methanation stage 40.3, and partially recycled to the other methanation stages 40.1 and 40.2 by the line 94, then divided into the lines 41 and 42, to increase the overall carbon efficiency of the process. Part of the carbon dioxide is also sent to the gasification stage of the plastic through the line 92.1 to be used in the realization of an atmosphere free of nitrogen in the plastic which is introduced into the reactor 10.

Furthermore, part of the $CO_2$ is also purged, as indicated by the dotted line 93 in FIG. 1.

The process gas from which the carbon dioxide was removed and which was also subjected to caustic washing has a $CO_2$ content reduced to less than 1 ppm, even of 0.5 ppm vol.

c) Finally, the process gas which leaves the unit 90 is compressed by means of a compressor-expander. After compression, the process gas is cooled to condense as much water as possible before being fed to drying beds with molecular sieves in which all the water is removed. These water removal and drying operations are indicated as a whole with reference numeral 100 in FIG. 1.

After $CO_2$ and water have been removed from the process gas, this is sent to a cryogenic separation section 110, comprising apparatuses known in the petrochemical industry, having the main function of separating the methane from the olefins and from the higher alkanes.

The bottom product of the cryogenic separation section 110 consists of liquid hydrocarbons (C2 and above) discharged through the line 112, which are sent to a further separation section 120.

The head product of the cryogenic separation section 110, taken from the line 114, consists mainly of methane with non-negligible percentages of hydrogen, CO and nitrogen, which is mostly recycled to the last methanation stage 40.3. through the line 114.1, and partly purged and possibly used as fuel for steam generation, as indicated by line 114.2. The purge function is mainly to avoid inert accumulation, mainly nitrogen, in the circuit relative to the OCM reactor. It is therefore clear that the fact of carrying out the stage A) of gasification with pure oxygen allows to: i) minimizing the quantity purged by cryogenic separation 110; ii) at the same time, reducing the amount of carbon ($CH_4$) lost in this purge; iii) increasing the carbon efficiency of the entire process described in the invention.

The bottom product of the cryogenic separation section 110, containing ethylene, ethane and other higher hydrocarbons, is sent to units for the separation of ethane, of propane, for the conversion of acetylene (generated as a by-product from the OCM reaction) to ethylene and ethane, designated overall with reference numeral 120. At the end of these treatments, Polymer Grade (PG C2) purity ethylene, is obtained, designated in FIG. 1 as $C_2^-$, and a background stream comprising hydrocarbons having three or more carbon atoms, designated as C3+. The C2/C3 recycling stream fed into the OCM reactor 70 via the line 115 comes from this separation section 120.

The C3+ stream from the bottom can be further fractionated to produce C3 products and streams of C4+ products, in particular for obtaining Chemical or Polymer Grade propylene.

Depending on market demand, it is possible to associate processes of the invention with known processes for ethylene dimerization and/or metathesis in order to transform (all or in part) the Polymer Grade ethylene produced in higher olefins (propylene/1-butene/1-hexene). Below is an example of an embodiment of the process according to the invention in a plant as shown in FIGS. 1-4.

EXAMPLE

Stage A)

7125 kg/h of recycled plastics, appropriately selected and minced, and 6555 kg/h of pure oxygen (99.5%) were fed to the gasification reactor 10. The plastic was introduced into the reactor together with a stream of $CO_2$ which has the purpose of creating a substantially nitrogen-free environment in the reactor.

The recycled plastic had the composition shown in Table 1.

TABLE 1

| Waste Plastic Composition | | |
|---|---|---|
| C | % weight | 79.5% |
| H | % weight | 13.1% |
| N | % weight | 0.2% |
| S | % weight | 0.1% |
| Cl | % weight | 0.0% |
| O | % weight | 4.5% |

TABLE 1-continued

| Waste Plastic Composition | | |
|---|---|---|
| Water | % weight | 0.7% |
| Ashes | % weight | 1.9% |

The gasification reaction was carried out at a pressure of 0.1 MPa and at a temperature of 1100° C.

12620.4 kg/h of synthesis gas having the composition shown in Table 2 were produced.

TABLE 2

| Gas Composition from Waste Plastic Gasification | | |
|---|---|---|
| $H_2$ | % mol | 53.48% |
| CO | % mol | 45.61% |
| $CO_2$ | % mol | 0.72% |
| $H_2O$ | % mol | 0.16% |
| $N_2$ | % mol | 0.01% |
| Ar | % mol | 0.02% |

The synthesis gas had an $H_2$/CO ratio of 1.17.

Stage B)

The synthesis gas obtained in stage A), after removing water by cooling (20) and compression (30) at 4 MPa, is sent to the first methanation stage 40.1 at a flow rate of 1262.4 kg/h, together with an external hydrogen flow of 1191.3 kg/h, at a pressure of 2.5 MPa.

The stage 40.1 methanation reactor is operated in the presence of the CRG™ catalyst of Johnson-Matthey.

The reactor output temperature was 418° C. and the pressure was 3.0 MPa.

An effluent flow rate of 156187.5 kg/h was recycled via line 45 to the inlet of the same reactor, while an amount of 8220.4 kg/h of effluent was sent to the second methanation stage 40.2. The cycle ratio was 19. The intermediate post-cooling effluent temperature was 240° C.

The effluent contained 83.35% molar of methane, 10.13% molar of $CO_2$, 0.42% molar of CO, 1.86% molar of hydrogen, 0.04% molar of argon and 4.20% molar of water.

The second methanation stage 40.2 was conducted in a reactor identical to that of stage 40.1, and at the same conditions of inlet temperature and pressure. A fresh hydrogen flow of 132.4 kg/h was fed to stage 40.2.

The reactor outlet temperature was 355° C.

The effluent flow rate of the second stage 40.2 was 8352.7 kg/h containing 82.2% molar of methane, 5.93% molar of $CO_2$, 0.33% molar of hydrogen, 0.04% molar of argon and 11.49 molar of water. The intermediate post-cooling effluent temperature was 253° C.

The SNG effluent is sent to a condensation stage 60 for removing the water. At the exit of this stage, the SNG temperature was 40° C. and the pressure was 3.0 MPa. The flow rate of the SNG was 7423 kg/h and its composition was: methane 92.43% molar, $CO_2$ 6.66% molar, hydrogen 0.37% molar and 0.49% molar of water.

The SNG effluent is sent to a third methanation stage 40.3, conducted in a reactor similar to that of stages 40.1 and 40.2.

A fresh hydrogen flow of 1320.9 kg/h was fed to stage 40.3.

The effluent flow rate of the third stage 40.3 was 110889 kg/h and contained 87.1% molar of methane, 1.56% molar of $CO_2$, 3.02% molar of nitrogen, 0.37% molar of hydrogen, 1.00% molar of argon and 6.96% molar of water. The effluent temperature was 243° C. and the pressure was 1.0 MPa.

Stage C)

The SNG effluent of the third methanation stage was heated to the temperature of 500° C. and sent to the methane oxidative coupling stage in the OCM reactor 70.

The OCM reactor 70 is operated in the presence of a heterogeneous catalyst based on mixed metal magnesium and manganese oxides, also comprising lithium and boron as additives and at least one element of the groups 4, 9, 12, 13 or combinations thereof, marketed by Siluria Technologies, Inc., arranged in a fixed bed in the upper zone Z1 of the reactor and the use of which allows a selectivity in ethylene greater than 50% and a conversion of methane greater than 20%. The temperature in zone Z1 of the reactor was 895° C. and the pressure was 0.7 MPa.

A flow of 17492 kg/h of oxygen was fed to the upper zone Z1 of the reactor 70 having a purity of 99.5% mol, for carrying out the OCM reaction. A flow of 1405 kg/h of C2/C3 recycling from stage D) was also fed to this upper zone Z1 through the line 115, containing 98.08 mol % of ethane and 1.92% molar of olefins, in order to carry out the conversion of ethane into ethylene by thermal cracking in the lower Z2 area of Post Bed Cracking (PBC).

From the OCM reactor 70, a flow rate of 128288 kg/h of a hot effluent 72 was discharged at the temperature of 876° C. containing 68.4% molar of methane, 5.4% molar of hydrogen, 4.07% molar of $CO_2$, 1.70% molar of CO, 2.70% molar of nitrogen, 1.87% molar of ethylene, 0.63% molar of ethane, 0.12% molar of propylene, the 0.89% molar of argon and 14.16% molar of water.

Stage D)

The hot effluent (process gas) from line 72 was compressed into a 3-stage centrifugal compressor at a final pressure of 4 MPa and cooled in water-cooled tube bundle heat exchangers. Water and condensed hydrocarbons were discharged via line 82 (FIG. 1).

The process gas was then sent to a $CO_2$ removal unit 90, which was discharged via line 92. A flow rate of 10378 kg/h of carbon dioxide thus removed from the process gas was recycled via line 92.2 to the third methanation stage 40.3.

A small fraction of this $CO_2$ is used to create a substantially nitrogen-free environment in the process of introducing the plastic to the first stage A).

A flow rate of carbon dioxide was also sent to the gasification stage of the plastic through the line 92.1 to be used in the realization of an atmosphere free of nitrogen in the plastic which is introduced into the reactor 10.

Furthermore, 2594 kg/h of $CO_2$ were purged, as indicated by the dotted line 93 in FIG. 1.

The process gas coming out of the unit 90 was compressed by a compressor-expander and cooled to condense as much water as possible before being fed to drying beds with molecular sieves in which all the water is removed, as indicated with reference numeral 100 in FIG. 1.

After $CO_2$ and water are removed from the process gas, this is sent to a cryogenic separation section 110, from which a bottom product consisting of 128 kg/h of 1,3-butadiene is discharged.

A flow consisting of 86.59% molar of methane, 6.74% molar of hydrogen, 3.40% molar of nitrogen, 2.12% molar of CO and 1.12% molar of argon was also taken through the line 114 and divided into two parts. Almost all of the stream, consisting of 91767 kg/h, was recycled to the last stage of methanation 40.3, through the line 114.1. A small part, consisting of 821 kg/h, was sent for purge in order to avoid inert accumulation, mainly nitrogen, in the circuit relating to the OCM reactor.

It is therefore clear that the fact of carrying out the stage A) of gasification with pure oxygen allows: i) minimizing the quantity purged by cryogenic separation 110; ii) at the same time, reducing the amount of carbon ($CH_4$) lost in this purge; iii) increasing the carbon efficiency of the entire process described in the invention.

The bottom product of the cryogenic separation section 110, containing ethylene, ethane and other higher hydrocarbons, was sent to unit 120 for the separation of ethane, propane and propylene. In this section, 3838 kg/h of ethylene, 342 kg/h of propylene and 1405 kg/h of ethane (recycled to OCM reactor) were separated and collected.

It therefore appears that the process of the invention allows the recycled plastic to be converted into olefins, in particular into ethylene and propylene, which can be repolymerized to polyethylene and polypropylene, or relative copolymers. The process therefore provides the monomers for the production of virgin polyolefins, i.e. polymers that have a higher economic value than that of recycled plastic.

From the point of view of the overall energy balance, it can be said that the process of converting plastics to olefins is favourable as it is based on exothermic reactions, therefore capable of generating heat used to produce steam and therefore energy for the operation of the various machines used in the plant, such as pumps and compressors, but also for the production of external hydrogen required for the methanation stage B), for example by water electrolysis.

The invention claimed is:

1. A process for converting plastics to olefins, comprising the steps of:
    a) gasifying said plastics into a synthesis gas by reacting said plastics with pure oxygen, wherein a total amount of pure oxygen and an amount of oxygen from said plastics is from 40% to 65% molar with respect to an amount of stoichiometric oxygen required for converting all the carbon contained in said plastics to carbon dioxide ($CO_2$);
    b) catalytically converting said synthesis gas into methane in at least three successive stages, wherein hydrogen is added to said synthesis gas in at least the first two stages of said at least three successive stages, said hydrogen having a degree of purity greater than 95%;
    c) catalytically converting said methane into olefins by oxidatively coupling said methane and forming an oxidative coupling effluent comprising olefins; and
    d) separating said olefins from the oxidative coupling effluent.

2. The process of claim 1, wherein said synthesis gas has a molar ratio of hydrogen to carbon monoxide ($H_2/CO$) greater than 1.

3. The process of claim 1, wherein step a) further comprises gasifying said plastics in a reactor, wherein carbon dioxide is introduced into the reactor for reducing a quantity of air in the reactor.

4. The process of claim 1, wherein step b) further comprises recycling a part of a gaseous mixture produced in a first stage of said at least three successive stages, wherein a recycle ratio of said recycled part varies from about 4 to 20 by weight.

5. The process of claim 4, wherein said recycle ratio of said recycled part varies from 8 to 18 by weight.

6. The process of claim 1, wherein a last stage of said at least three successive stages of step b) is operated with a molar ratio of hydrogen to carbon ($H_2/C$) between 1.2 and 3.

7. The process of claim 1, wherein step b) comprises four successive stages wherein hydrogen is added to said synthesis gas in at least the first three stages of said four successive stages.

8. The process of claim 1, wherein step c) further comprises catalytically converting a mixture, the mixture containing at least 85% molar of said methane.

9. The process of claim 1, wherein step c) produces a gaseous mixture, said gaseous mixture comprising said olefins and carbon dioxide.

10. The process of claim 9, wherein step a) further comprises introducing carbon dioxide along with said plastics to a gasification reactor, said carbon dioxide producing a substantially nitrogen-free atmosphere in said reactor.

11. A process for converting plastics to olefins, comprising the steps of:
  a) selecting said plastics, said plastics comprising:
    a carbon content greater than 45% by weight;
    a hydrogen content greater than 5% by weight; and
    an oxygen content less than 20% by weight;
  b) gasifying said plastics into a synthesis gas in a reactor, by:
    reacting said plastics with pure oxygen, wherein a total amount of pure oxygen and an amount of oxygen from said plastics is from 40% to 65% molar with respect to an amount of stoichiometric oxygen required for converting all the carbon contained in said plastics to carbon dioxide (CO2); and
    wherein carbon dioxide is introduced into the reactor for reducing a quantity of air in the reactor;
  c) catalytically converting said synthesis gas into methane in at least three successive stages, wherein hydrogen is added to said synthesis gas in at least the first two stages of said at least three successive stages, said hydrogen having a degree of purity greater than 95%;
  d) catalytically converting said methane into said olefins by oxidatively coupling said methane and forming an oxidative coupling effluent comprising olefins; and
  e) separating said olefins from the oxidative coupling effluent.

12. The process of claim 11, wherein step a) further comprises shredding and reducing said plastics into plastic flakes.

13. The process of claim 11, wherein said plastics further comprise:
  a nitrogen content, a halogen content, and a sulfur content less than 3% by weight;
  an inert content less than 20% by weight; and
  a moisture content less than 10% by weight.

14. The process of claim 11, wherein said synthesis gas has a molar ratio of hydrogen to carbon monoxide ($H_2/CO$) greater than 1.

15. The process of claim 11, wherein step c) further comprises recycling a part of a gaseous mixture produced in a first stage of said at least three successive stages, wherein a recycle ratio of said recycled part varies from about 4 to 20.

16. The process of claim 11, wherein a last stage of said at least three successive stages of step c) is operated with a molar ratio of hydrogen to carbon ($H_2/C$) between 1.2 and 3.

17. The process of claim 11, wherein step c) comprises four successive stages, wherein said hydrogen is added to said synthesis gas in at least the first three stages of said four successive stages.

18. The process of claim 11, wherein step d) further comprises catalytically converting a mixture, the mixture containing at least 85% molar of said methane.

19. The process of claim 11, wherein step d) produces a gaseous mixture, said gaseous mixture comprising said olefins and carbon dioxide ($CO_2$), and step b) further comprises introducing carbon dioxide along with said plastics to a gasification reactor, said carbon dioxide producing a substantially nitrogen-free atmosphere in said reactor.

20. A process for converting plastics to olefins, comprising the steps of:
  a) selecting said plastics, and shredding and reducing said plastics into plastic flakes, said plastics comprising:
    a carbon content greater than 45% by weight;
    a hydrogen content greater than 5% by weight;
    an oxygen content less than 20% by weight;
    a nitrogen content, a halogen content, and a sulfur content less than 3% by weight;
    an inert content less than 20% by weight; and
    a moisture content less than 10% by weight;
  b) gasifying said plastics into a synthesis gas in a reactor by:
    reacting said plastics with pure oxygen, wherein a total amount of pure oxygen and an amount of oxygen from said plastics is from 40% to 65% molar with respect to an amount of stoichiometric oxygen required for converting all the carbon contained in said plastics to carbon dioxide ($CO_2$); and
    gasifying said plastics in a reactor, wherein carbon dioxide is introduced into the reactor for reducing a quantity of air in the reactor;
  c) catalytically converting said synthesis gas into methane in four successive stages, wherein hydrogen is added to said synthesis gas in at least the first three stages of said four successive stages, said hydrogen having a degree of purity of greater than 95%;
  d) catalytically converting said methane into said olefins by oxidatively coupling said methane and forming an oxidative coupling effluent comprising olefins; and
  e) separating said olefins from the oxidative coupling effluent.

* * * * *